United States Patent [19]

Brouwer et al.

[11] Patent Number: 4,675,044
[45] Date of Patent: Jun. 23, 1987

[54] 3-ARYL-5,6-DIHYDRO-1,4,2-OXATHIAZINES AND THEIR OXIDES

[75] Inventors: Walter G. Brouwer, Guelph, Canada; Allyn R. Bell, Cheshire, Conn.; Allen R. Blem, Cheshire, Conn.; Robert A. Davis, Cheshire, Conn.

[73] Assignees: Uniroyal Chemical Company, Inc., Middlebury, Conn.; Uniroyal Ltd., Don Mills, Canada

[21] Appl. No.: 794,197

[22] Filed: Nov. 1, 1985

Related U.S. Application Data

[60] Division of Ser. No. 531,362, Sep. 12, 1983, Pat. No. 4,569,690, which is a continuation-in-part of Ser. No. 425,739, Sep. 28, 1982, abandoned.

[51] Int. Cl.$^4$ ............................................. A01N 43/88
[52] U.S. Cl. ......................................................... 71/73
[58] Field of Search ...................................... 71/73, 74

[56] References Cited

U.S. PATENT DOCUMENTS 2,845,339  7/1958  Bluestone ................................ 71/73
3,920,438 11/1975  Brewer et al. ........................... 71/73

FOREIGN PATENT DOCUMENTS 071317  2/1984  Japan .

OTHER PUBLICATIONS

S. Hoff et al, Tetrahedron Letters, No. 52, pp. 5267–5268, (1972).
Bauer et al, J. Org. Chem., vol. 30, pp. 949–951, (1965).

Primary Examiner—Catherine L. Mills
Attorney, Agent, or Firm—William E. Dickheiser

[57] ABSTRACT

Disclosed are derivatives of 3-aryl-5,6-dihydro-1,4,2-oxathiazines and their oxides for use as herbicides, fungicides, plant dessicants and defoliants in agricultural and biocidal applications. Also disclosed are methods of making these compounds.

9 Claims, No Drawings

3-ARYL-5,6-DIHYDRO-1,4,2-OXATHIAZINES AND THEIR OXIDES

This is a division of U.S. patent application Ser. No. 531,362 filed Sept. 12, 1983, now U.S. Pat. No. 4,569,690, which is a continuation-in-part of U.S. patent application Ser. No. 425,739 filed Sept. 28, 1982 and now abandoned.

This invention relates to derivatives of 3-aryl-5,6-dihydro-1,4,2-oxathiazines and their oxides, and to the use of such derivatives as herbicides, fungicides, and plant dessicants and defoliants. The invention also relates to methods of preparing these chemicals.

Dihydro 1,4,2-oxathiazines are little known in the chemical literature. A multi-substituted compound, N-(5,6-dihydro-5,6dimethyl-3-phenyl-1,4,2-oxathiazine-6yl)acetamide, was reported in Tetrahedron Letters, 1972, p. 5267, and a tetrahydro compound was described in J. Org. Chem. 30: 949 (1965). However, no utility was disclosed for these compounds.

The chemicals of this invention are represented by the general formulae below, and possess herbicidal activity, fungicial activity and plant desiccating and defoliating activities.

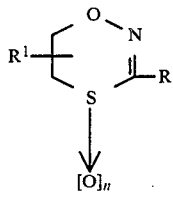

wherein n is 0, 1 or 2, $R^1$ is hydrogen, $C_1$–$C_4$ linear or branched alkyl or benzyl, and R has one of the following values:
 phenyl or naphtyl;
 phenyl substituted with 1 or 2 of the following groups:
  hydroxyl
  halo
  $C_1$–$C_{12}$ alkyl
  $C_5$–$C_6$ cycloalkyl
  trihalomethyl
  phenyl
  $C_1$–$C_5$ alkoxy or alkylthio
  tetrahydropyranyloxy
  phenoxy
  $C_2$–$C_5$ alkylcarbonyl
  phenylcarbonyl
  $C_1$–$C_4$ alkylsulfinyl
  $C_1$–$C_4$ alkylsulfonyl
  carboxy or its alkali metal salt
  $C_2$–$C_5$ alkoxycarbonyl
  $C_2$–$C_5$ alkylaminocarbonyl
  phenylaminocarbonyl
  tolylaminocarbonyl
  morpholinocarbonyl
  amino
  nitro
  cyano or
  dioxolanyl;
 pyridinyl;
 thienyl provided n is not 2;
 furanyl;
 furanyl substituted with 1 to 3 of the following groups:
  $C_1$–$C_4$ alkyl and
  $C_2$–$C_5$ alkoxycarbonyl.

In preferred compounds of the foregoing formula, $R^1$ is hydrogen or $C_1$–$C_4$ linear or branched alkyl and R has one of the following values:
 phenyl;
 phenyl substituted with 1-2 of the following groups:
  F, Cl, Br, except not 2-Cl or 2,4-$Cl_2$ if n is 2
  $C_1$–$C_4$, except p-t-alkyl if n is zero
  $CF_3$
  phenyl except if n is 2
  $C_1$–$C_5$ alkoxy
  $C_2$–$C_5$ alkylcarbonyl
  $C_2$–$C_5$ alkoxycarbonyl except 4-alkoxycarbonyl if n is zero
  amino
  nitro or
  cyano;
 3- or 4-pyridinyl provided n is not 2
 thienyl provided n is not 2;
 furanyl;
 furanyl substituted with 1 to 3 of the following groups:
  methyl or
  $C_2$–$C_3$ alkoxycarbonyl.

In more preferred compounds of the above formula, $R^1$ is hydrogen or methyl and R has one of the following values:
 phenyl provided n is not 2;
 phenyl substituted with 1 or 2 of the following groups:
  F, Cl, Br, but not 2-Cl or 2,4-$Cl_2$ if n is 2
  n-$C_1$–$C_4$alkyl
  $CF_3$
  $C_1$–$C_2$ alkoxy
  $C_2$–$C_5$ alkylcarbonyl, provided n is 1
  $C_2$–$C_3$ alkoxycarbonyl provided n is 1 or 2
  nitro or
  cyano;
 3- or 4-pyridinyl provided n is 0 or 1;
 thienyl provided n is 0 or 1;
 furanyl;
 furanyl substituted with 1 to 3 methyl groups, provided n is 1 or 2.

Compounds of the invention may be used for control of various grasses and broadleaved weeds including pigweed (*Amaranthus retroflexus* L.), velvetleaf (*Abutilon theophrasti* Medic.), jimsonweed (*Datura stramonium* L.), tall morning-glory (*Ipomoea purpurea* (L.) Roth), barnyardgrass (*Echinochloa crusgalli* (L.) Beauv.), green foxtail (*Setaria viridis* (L.) Beauv.) giant foxtail (*Setaria faberi* Herrm.), crabgrass (*Digitaria ischaemum* (Schreb.) Muhl.) and switchgrass (*Panicum virgatum* L.).

Chemical harvest aids are used for a wide variety of primary effects, including the defoliation of the crop plant; the desication of its leaves, stems, and other aerial organs; the control of late-season regrowth (e.g. cotton); the concentration of crop maturity providing more efficient harvesting.

Under normal conditions, many crop plants do not mature uniformly or in a timely fashion, so that efficient, optimum harvest is difficult, either due to equipment scheduling or to weather. Crops such as cotton, potato, sunflower, seed legumes and other oilseed crops require either desiccation or defoliation before harvest can be effectively accomplished. Cotton is an example of a crop with a long history of successful harvest aid use. When cotton is adequately defoliated, mechanical pickers can operate more effectively. If the crop is not defoliated, the leaves can interfere with the picking mechanism. Also, leaves can contaminate the cotton lint with trash or green stain, which reduces the quality of the fiber or reduces the efficiency of the ginning process. Likewise, potato vines need to be desiccated for efficient mechanical digging. In addition, upon desiccation of potato leaves and haulms, the tuber skin matures and becomes less susceptible to damage from the digger and post-harvest handling. Seed legumes and sunflowers are also mechanically harvested, and this process is facilitated if the leaves are removed or desiccated. As with cotton and potato, such defoliation or desiccation also ripens the seed uniformly, accelerates the rate of fruit maturation, and conditions the pod or head for easy harvest.

Compounds of this invention have been found to have surprising utility as harvest aid chemicals. Specifically, when applied to the foilage of crop species, they cause desiccation and/or defoliation of the leaves, can cause desirable changes in the fruiting form (e.g. cotton boll), and may alter the re-growth of the plant.

Applications of the compounds may be in the form of aqueous solutions or suspensions applied to the target tissue. Compounds of this invention may be used alone, in combination with one or more other oxathiazine derivative described here, or as a tank mix with other harvest aid chemical compounds or spray adjuvants (such as surface-active agents, stickers, emulsifiers, or extenders).

In addition, the chemicals described for this invention possess antifungal properties which are useful for the control of plant diseases such as Rice Blast, Bean Rust, Tomato Early Blight, Cercospora Leaf Spot or similar diseases. Growth inhibition tests indicate a broad spectrum of activity against other disease-producing fungi such as Alternaria, Sclerotium, Piricularia, Pythium, Phytophthora, Fusarium.

Two methods of synthesizing the chemicals of this invention have been discovered. One of these is outlined in Scheme I below and utilizes aromatic aldehydes as starting materials.

SCHEME I $$R-\overset{Cl}{\underset{}{C}}=NOH + ClCH_2CH_2SH \xrightarrow[\text{(2 equivalents)}]{\text{base}} \underset{\underset{\text{Ia}}{(O)_n}}{\overset{O\diagdown N}{\underset{S}{\bigcirc}}\hspace{-2pt}R}$$

II    III n = zero

N-hydroxyarylcarboximidoyl chloride (II) is treated with 2-chloroethanethiol in the presence of two equivalents of base or suitable hydrogen chloride scavenger to produce 3-aryl-5,6-dihydro-1,4,2-oxathiazine (I, n=0). The II intermediate may be readily made by known methods by converting an aldehyde of the formula RCHO to its corresponding oxime (RCH=NOH) in the presence of $H_2NOH$ and subsequent chlorination with chlorine or t-butyl hypochlorite in methylene chloride or chloroform as the solvent. If only one equivalent of base is used, the intermediate 2-chloroethyl N-hydroxybenzene-carboximidothioate derivative is isolated. This intermediate will give the oxathiazine when treated with a base.

Oxidation of oxathiazines with peroxyacetic acid or m-chloroperoxybenzoic gives the oxides (I, n=1 or 2).

Scheme II below outlines the second method of preparation, which uses arylcarbodithioate esters.

SCHEME II

Step 1

$$R-CS_2CH_2CH_3 \xrightarrow{H_2NOH} R-\overset{S}{\underset{}{\overset{\|}{C}}}-NHOH \rightleftharpoons R-\overset{SH}{\underset{}{\overset{|}{C}}}=NOH$$

IV    Va    Vb

Step 2

$$\underset{\text{(2 equivalents)}}{\overset{X\hspace{10pt}X}{\underset{}{\overset{|\hspace{10pt}|}{R^1-CH-CH-R^2}}} \xrightarrow{\text{base}}} \underset{\underset{\text{Ib}}{(O)_n}}{\overset{R^1\diagdown\hspace{-2pt}\diagup O\diagdown N}{\underset{S}{R^2\diagup\hspace{-2pt}\diagdown}}\hspace{-2pt}R}$$

X = halogen (Cl, Br, I)
n = zero
$R^1$ and $R^2$ = halogen, $C_1$-$C_4$ alkyl or benzyl provided at least one of $R^1$ and $R^2$ is hydrogen Treatment of a carbodithioate ester (IV) with hydroxylamine results in the liberation of ethyl mercaptan and the formation of N-hydroxyarylthioamide (Va) which enolises to N-hydroxyarylcarboximidothioic acid (Vb). Formation of the oxathiazine is then accomplished by reacting with vicinal dihaloalkane, $$\underset{X\hspace{18pt}X}{\overset{R^1CH-CH_2}{\underset{}{\overset{|\hspace{18pt}|}{}}}}$$

($R^1$ and X as previously described) in the presence of two equivalents of base. A minor impurity is sometimes obtained in this reaction. For example, when two molecules of N-hydroxycarboximidothioic acid (Vb) react with one molecule of 1,2-dibromoethane, 1,2,-ethanediyl bis(N-hydroxyarylcarboximidothioate) is produced and can be extracted from the reaction by washing with dilute aqueous sodium hydroxide.

In Scheme I, the reaction of compound II with compound III for the preparation of the desired oxathiazine of this invention may be carried out at a temperature of minus 10° to plus 20° C. Usually, the reaction takes about 0.5–6 hours for completion but ordinarily does not take longer than 3 hours.

In Scheme II, the Step I reaction is performed at from 0° to 30° C., usually at 10°–25° C., and it may take 0.5–2 hours, generally 0.5–1 hour to form the Va/Vb equilibrium product. In Step 2, a temperature of 0°–100° C. may be employed although a 20°–80° C. temperature range is more preferred. The reaction usually takes from 0.5 to 5 hours, but in many cases completion can be obtained within 3 hours. As solvents, $C_1$–$C_{10}$ aliphatic alcohols may be used or aprotic solvents such as dimethylformamide or dimethylsulfoxide.

If so desired, intermediate compounds suitable for making the chemicals of this invention may be prepared having the structural formula $RC(=NOH)SCH_2CH_2Cl$ by using Scheme I of this invention wherein R has the meanings of claim 1, $R^1$ is hydrogen and n is 0, using only one equivalent of base such as alkali metal $C_1$–$C_{10}$ alkoxide, alkylamines, alkanolamines pyridine, morpholine and similar organic bases.

The preparation of the compounds can best be illustrated by the following specific examples.

Compound numbers are in parenthesis (c.f. Tables 1 to 4).

EXAMPLE 1

2-Chloroethyl 2-chloro-N-hydroxybenzenecarboximidothioate

2-Chlorobenzaldoxime (46.7 g, 0.3 mol) in chloroform (350 ml) was cooled and stirred in an ice/salt bath. Chlorine gas was bubbled into the reaction until an excess was present. Excess chlorine and solvent were removed and the remaining 2-chloro-N-hydroxybenzenecarboximidoyl chloride dissolved in ether (250 ml). Solutions of triethylamine (30.3 g, 0.3 mol) in ether (50 ml) and 2-chloroethanethiol (29 g, 0.3 mol) in ether (50 ml) were added simultaneously with stirring and cooling. After the addition, the reaction was allowed to warm to room temperature and left overnight. Water was added, and the ether layer was washed with additional water, then dried with anhydrous magnesium sulphate. Evaporation left a white solid, 2-chloroethyl 2-chloro-N-hydroxybenzenecarboximidothioate, m.p. 115°–117° C., (Found: C, 43.29; H, 3.58; N, 5.59. $C_9H_9Cl_2NOS$ requires C, 43.21; H, 3.62; N, 5.60).

The following compounds of this type were prepared in a similar manner.

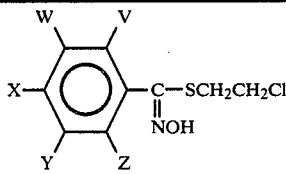

| V | W | X | Y | Z | m.p. °C. |
|---|---|---|---|---|---|
| H | H | Cl | H | H | 110–117 |
| Cl | H | Cl | H | H | 104–106 |
| H | H | $CH_3$ | H | H | 118–119 |
| $CH_3$ | H | H | $CH_3$ | H | 86–96 |

EXAMPLE 2

3-(2-Chlorophenyl)-5,6-dihydro-1,4,2-oxathiazine (3)

2-Chloroethyl 2-chloro-N-hydroxybenzenecarboximidothioate (25 g, 0.1 mol) was added to a cold solution of sodium (2.3 g) in ethanol (150 ml). An exotherm was observed. The reaction was left at room temperature overnight, then the ethanol was removed, the product extracted with ether, the ether solution washed with water, dried and evaporated to leave an oil. Distillation b.p. 121° C. at 0.02 mm (2.67 pa) gave an oil which solidified, 3-(2-chlorophenyl)-5,6-dihydro-1,4,2-oxathiazine, m.p. 51°–52° C. (Found: C, 50.30; H, 3.73; N, 6.57. $C_9H_8ClNOS$ requires C, 50.58; H, 3.77; N, 6.55).

EXAMPLE 3

5,6-Dihydro-3-(4-pyridinyl)-1,4,2-oxathiazine (11)

4-Pyridinecarboxaldehyde oxime (30.6 g, 0.25 mol) was chlorinated in chloroform (350 ml) as described in Example 1 to produce N-hydroxy-4-pyridine-carboximidoyl chloride which was suspended in ether (500 ml) containing 2-chloroethanethiol (26.9 g, 0.25 mol). With ice bath cooling, triethylamine (5.1 g, 0.5 mol) was added dropwise. After the addition, water was made, the suspended solid, crude 2-chloroethyl N-hydroxy-4-pyridinecarboximidothioate was collected on a filter and dried. This crude ester was added to a solution of sodium ethoxide (from 5.75 g sodium in 500 ml ethanol), and the reaction mixture stirred for 4 hours. Water was added and the product was extracted with ether to give 5,6-dihydro-3-(4-pyridinyl)-1,4,2-oxathiazine, mp 80°–82° C., (found: C, 53.16; H, 4.56; N, 15.07. $C_8H_8N_2OS$ requires C, 53.33; H, 4.48; N, 15.55).

EXAMPLE 4

5,6-Dihydro-3-[3-trifluoromethyl)phenyl]-1,4,2-oxathiazine (45)

Ethyl 3-(trifluoromethyl)benzenecarbodithioate (24.7 g, 0.1 mol) was dissolved in ethanol (50 ml) in which was suspended hydroxylamine hydrochloride (7 g, 0.1 mol). With stirring, triethylamine (10.1 g, 0.1 mol) in ethanol (25 ml) was added dropwise. After 5 hours, ethyl mercaptan was removed under reduced pressure through a KOH scrubber. 1,2-Dibromoethane (19 g, 0.1 mol) was added to the reaction mixture followed by dropwise addition of triethylamine (30 ml) in ethanol (50 ml). A white precipitate formed. After the addition was complete, the reaction mixture was warmed until it was homogenous, then left at room temperature overnight. Water was added, the product extracted into ether, the ether solution washed with dilute sodium hydroxide (2N approx.), then water, dried over anhydrous magnesium sulphate and evaporated to leave an oil which was distilled to give 5,6-dihydro-3-[3-(trifluoromethyl)phenyl]-1,4,2-oxathiazine, bp 113°/0.2 mm.

EXAMPLE 5

5,6-Dihydro-3-(2-furanyl)-1,4,2-oxathiazine (31)

Methyl 2-furancarbodithioate (30 g, 0.2 mol) was converted to 5,6-dihydro-3-(2-furanyl)-1,4,2-oxathiazine, an oil, bp 128°–129° C. at 1.3 mm (173 Pa), (preparation similar to Example 4). The sodium hydroxide wash from the ether extract was acidified. An amber oil separated out and on standing, solidified. This solid was collected, washed with ether, dried and found to be 1,2-ethandiylbis(N-hydroxy-2-furancarboximidothioate), mp 147°–150° C. (Found: C, 45.80; H, 4.08; N, 8.62. $C_{12}H_{12}N_2O_4S_2$ requires C, 46.16; H, 3.87; N, 8.97.)

EXAMPLE 6

5,6-Dihydro-3-(3-fluorophenyl)-1,4,2-oxathiazine, 4-oxide (28)

5,6-Dihydro-3-(3-fluorophenyl)-1,4,2-oxathiazine (19.7 g, 0.1 mol) was dissolved in chloroform, 50 ml). 3-Chloroperoxybenzoic acid (21 g) dissolved in chloroform (200 ml) was added dropwise at such a rate that the temperature of the reaction mixture remained at between 25° to 30° C. After the addition was complete, the reaction was left stirring at room temperature overnight. Saturated aqueous sodium bicarbonate was added and stirred until all gassing ceased. The chloroform solution was washed with water, dried over anhydrous magnesium sulphate and evaporated to leave a solid which was recrystallised from ether/ligroin, to give 5,6-dihydro-3-(3-fluorophenyl)-1,4,2-oxathiazine 4-oxide, mp 79° C.

EXAMPLE 7

5,6-Dihydro-3-(3-chlorophenyl)-1,4,2-oxathiazine, 4-oxide (84)

5,6-Dihydro-3-(3-chlorophenyl)-1,4,2-oxathiazine (21.4 g, 0.1 mol) in methylene chloride (50 ml) was cooled with ice water. 3-Chloroperoxybenzoic acid (21 g, 85%) in methylenechloride (150 ml) was added dropwise the reaction was stirred and the temperature maintained at 10° C. After the addition, the reaction was brought to ambient temperature and stirred overnight. After washing with aqueous sodium bicarbonate, water and then drying over anhydrous magnesium sulphate, evaporation of the solvent left a solid which was washed with ether and dried to leave 5,6-dihydro-3-(3-chlorophenyl)-1,4,2-oxathiazine, 4-oxide, mp 112°–4° C. (Found: C, 47.03; H, 3.43; N, 6.21. $C_9H_8ClNO_2S$ requires C, 47.07, H, 3.51, N, 6.09.)

EXAMPLE 8

3-(2,6-Dichlorophenyl)-5,6-dihydro-1,4,2-oxathiazine, 4,4-dioxide (56)

3-(2,6-Dichlorophenyl)5,6-dihydro-1,4,2-oxathiazine was oxidised as in Example 6 except that two equivalents of 3-chloroperoxybenzoic acid were used. Thus, 3-(2,6-dichlorophenyl)-5,6-dihydro-1,4,2-oxathiazine 4,4-dioxide, mp 180°–182° C. was prepared. (Found: C, 38:40; H, 2.56; N, 5.02. $C_9H_7Cl_2NO_3S$ requires C, 38.58; H, 2.51; N, 5.00.)

EXAMPLE 9

3-(3-Chlorophenyl)-5,6-dihydro-1,4,2-oxathiazine (26)

Ethyl 3-chlorobenzenecarbodithioate (106 g, 0.5 mol) and ethanol (400 ml) was treated with finely powdered hydroxylamine hydrochloride (36 g, 0.5 mol, 97%) with stirring, triethylamine (50.5 g, 70 ml, 0.5 mol) was added dropwise. A slight exotherm was observed. After the addition, the reaction was stirred for 1½ hours. Ethyl mercaptan was removed using a scrubber and vacuum trap. 1,2-Dibromoethane (95 g, 0.5 mol) was added to the reaction and with stirring, triethylamine (101 g, 140 ml, 1 mol) added dropwise. The initial red colour was completely discharged. When the addition was complete, the reaction was refluxed for 1 hour, cooled to room temperature and the solvent removed to leave a solid. Water was added, the product extracted into ether which was subsequently washed successively with water, 5% potassium hydroxide, water and then dried over anhydrous magnesium sulphate. After evaporation, a white solid remained, 3-(3-chlorophenyl)-5,6-dihydro-1,4,2-oxathiazine, mp 65° C.

EXAMPLE 10

3-(3-Fluorophenyl)-5,6-dihydro-1,4,2-oxathiazine (27)

2-Chloroethyl 3-fluoro-N-hydroxybenzenecarboximidothioate was made in a manner similar to that described in Example 1 using the following materials:
3-Fluorobenzaldehyde oxime (27.8 g, 0.2 mol)
2-Chloroethanethiol (21.5 g, 0.2 mol)
Triethylamine (40.8 g, 0.4 mol)
Ether (400 ml)

Cyclisation of 2-chloroethyl 3-fluoro-N-hydroxybenzenecarboximidothioate was accomplished as described in Example 2 using sodium (4.6 g) in ethanol (300 ml) to give 3-(3-fluorophenyl)-5,6-dihydro-1,4,2-oxathiazine, mp 47°–9° C. (Found: C, 54.66; H, 4.13; N, 7.07. $C_9H_8FNOS$ requires C, 54.81; H, 4.09; N, 7.10).

EXAMPLE 11

5,6-Dihydro-3-(3-nitrophenyl)-1,4,2-oxathiazine (12)

5,6-Dihydro-3-(3-nitrophenyl)-1,4,2-oxathiazine, mp 114°–5° C., was prepared in a manner as described in Example 9 using the following materials:
Methyl 3-nitrobenzenecarbodithioate, (117 g, 0.55 mol)
Ethanol (250 ml)
Hydroxylamine hydrochloride (40 g, 0.55 mol)
1,2-Dibromomethane (40 ml)
Triethylamine (80 ml) and a further (160 ml).

EXAMPLE 12

3-(4-Chlorophenyl)-5,6-dihydro-1,4,2-oxathiazine (1)

2-Chloroethyl 4-chloro-N-hydroxybenzenecarboximidothioate (2.5 g, 0.01 mol) was cyclised with sodium (0.23 g) in ethanol (25 ml) as described in Example 2. 3-(4-Chlorophenyl)-5,6-dihydro-1,4,2-oxathiazine, mp 80.5°–81.5° C., was isolated. (Found: C, 50.16; H, 4.24; N, 6.44. $C_9H_8ClNOS$ requires C, 50.58; H, 3.77; N, 6.55.)

EXAMPLE 13

(3-(4-Bromophenyl)-5,6-dihydro-1,4,2-oxathiazine (70 )

3-(4-Bromophenyl)-5,6-dihydro-1,4,2-oxathiazine, mp 114°–5° C., was made as described in Example 9 using the following materials:
Ethyl 4-bromobenzenecarbodithioate (130.5 g, 0.5 mol)
Ethanol (500 ml)
Hydroxylamine hydrochloride (97%) (36 g, 0.5 mol)
1,2-dibromoethane (45 ml)
Triethylamine (72 ml) and a further (140 ml).

EXAMPLE 14

3-(3,5-dichlorophenyl)-5,6-dihydro-1,4,2-oxathiazine (64)

3-(3,5-Dichlorobenzenecarbodithioate (50 g, 0.2 mol), mp 88°–9° C.
Ethanol 250 ml
Hydroxylamine hydrochloride 14.5 g, 0.2 mol
Triethylamine (28 ml) in ethanol (30 ml)
1,2-dibromoethane (25 ml)
Triethylamine (56 ml)

EXAMPLE 15

5,6-Dihydro-3-(2-thienyl)-1,4,2-oxathiazine (37)

5,6-Dihydro-3-(2-thienyl)-1,4,2-oxathiazine, mp 86°–89° C., was made as described in Example 9 using the following materials:
Methyl 2-thiophenecarbodithioate (35 g, 0.2 mol)
Ethanol (100 ml)
Hydroxylamine hydrochloride (14 g, 0.2 mol)
1,2-Dibromoethane (37.6 g, 0.2 mol)
Triethylamine (28 ml) and a further (56 ml)

EXAMPLE 16

Ethyl 4-(5,6-dihydro-1,4,2-oxathiazine-3-yl)benzoate (80)

Ethyl 4-(5,6-dihydro-1,4,2-oxathiazine-3-yl)benzoate, mp 69°–70° C. was prepared as outlined in Example 9 using the following:
Ethyl 4-[(methylthio)thioxomethyl]benzoate (83 g, 0.35 mol)
Ethanol (200 ml)
Hydroxylamine hydrochloride (97%) (25 g, 0.35 mol)
Triethylamine (50 ml) in ethanol (50 ml)
1,2-Dibromoethane (30 ml)
Triethylamine (100 ml).

EXAMPLE 17

3-(3-Chlorophenyl)-5,6-dihydro-5-(or 6)-methyl-1,4,2-oxathiazine (92)

3-(3-Chlorophenyl)-5,6-dihydro-5-(or 6)-methyl-1,4,2-oxathiazine, bp 145° C. at 0.25 mm (33.3 Pa), was prepared as described in Example 9 using the following:
Ethyl 3-chlorobenzenecarbodithioate (43.2 g, 0.2 mol)
Ethanol 200 (ml)
Hydroxylamine hydrochloride (14.5 g, 0.2 mol)
1,2-Dibromopropane (40.5 g, 0.2 mol)
Triethylamine (28 ml) and a further (56 ml).

EXAMPLE 18

[(3-(5,6-Dihydro-1,4,2-oxathiazine-3-yl)]-N-phenylbenzamide (100)

3-(5,6-Dihydro-1,4,2-oxathiazine-3-yl)benzoic acid (15 g, 0.07 mol) was suspended in methylene chloride (200 ml). Thionyl chloride (10 ml) was added and the reaction was refluxed until homogeneous and all gassing had ceased. The solvent was removed, the remaining oil was taken up in methylene chloride and treated portionwise with aniline (12.5 g, 0.12 mol). An exotherm was observed. After several hours, water was added, the organic material separated, washed successively with water, aqueous bicarbonate, dilute hydrochloric acid, water and then dried over anhydrous magnesium sulphate. Evaporation of the solvent left a solid which was recrystallised from ethanol to give crystals of 3-(5,6-dihydro-1,4,2-oxathiazin-3-yl)-N-phenylbenzamide, mp 149°–150° C. (Found: C, 64.65; H, 4.92; N, 9.65. $C_{16}H_{14}N_2O_2S$ requires C, 64.42; H, 4.73; N, 9.39).

TABLE 1

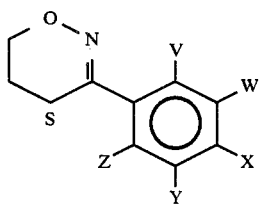

| COMPOUND | V | W | X | Y | Z | m.p. °C. or bp. |
|---|---|---|---|---|---|---|
| 1 | H | H | Cl | H | H | 80.5–81.5 |
| 3 | Cl | H | H | H | H | 51–52, 121 at 0.02 mm (2.67 Pa) |
| 6 | Cl | H | Cl | H | H | 137–141° at 0.05 mm (6.67 Pa) |
| 8 | H | H | $CH_3$ | H | H | 125–128° 1.5 mm (200 Pa) |
| 9 | $CH_3$ | H | H | $CH_3$ | H | 139–140° at 0.4 mm (53.3 Pa) |
| 12 | H | $NO_2$ | H | H | H | 114–115 |
| 13 | H | Cl | Cl | H | H | 77–78 |
| 16 | $CH_3$ | H | H | H | H | 160 at 3 mm (400 Pa) |
| 18 | H | H | H | H | H | 47–49 |
| 26 | H | Cl | H | H | H | 65 |
| 27 | H | F | H | H | H | 47–49 |
| 30 | H | $CH_3$ | H | H | H | 52–54 |
| 34 | H | H | $OCH_3$ | H | H | 91–92 |
| 35 | H | $OCH_3$ | H | H | H | oil |
| 39 | H | H | F | H | H | 46–48; 90° at 0.05 mm (6.67 Pa) |
| 47 | Cl | H | H | H | F | oil |
| 48 | H | H | CN | H | H | 115–118 |
| 51 | H | H | $COCH_3$ | H | H | 128–129 |
| 54 | Cl | H | H | H | Cl | 96–97 |
| 60 | H | H | $OC_6H_5$ | H | H | 98–100 |
| 62 | H | H | $COC_6H_5$ | H | H | 125–126 |
| 63 | H | H | $O(CH_2)_3CH_3$ | H | H | 96–7 |
| 64 | H | Cl | H | Cl | H | 88–9 |
| 69 | H | H | $C(CH_3)_3$ | H | H | 86–90 |
| 70 | H | H | Br | H | H | 114–5 |
| 71 | H | H | $(CH_2)_3CH_3$ | H | H | Oil |
| 78 | H | H | $CF_3$ | H | H | 110–1 |
| 80 | H | H | $CO_2CH_2CH_3$ | H | H | 69–70 |
| 79 | H | H | $CO_2H$ | H | H | 225 |
| 87 | H | $CO_2CH_3$ | H | H | H | 65–6 |
| 45 | H | $CF_3$ | H | H | H | 113° at 0.2 mm (26.7 Pa) |
| 88 | H | H | $C_6H_5$ | H | H | 147–150 |
| 89 | H | Br | H | H | H | 95–97 |
| 93 | H | $CO_2H$ | H | H | H | 168–171 |
| 98 | H | H | $SCH_3$ | H | H | 104–105 |
| 99 | H | H | $CONH-C_6H_4-2-CH_3$ | H | H | 183–185 |
| 100 | H | $CONHC_6H_5$ | H | H | H | 149–150 |
| 101 | H | H | $SOCH_3$ | H | H | 116–117 |
| 107 | H | H | O—2-Tetrahydropyranyl | H | H | 93–94 |
| 108 | H | H | $OCH_2CH_3$ | H | H | 95–96 |
| 109 | H | H | $OC_5H_{11}$ | H | H | 93–95 |
| 92(2) | H | Cl | H | H | H | 145/0.25 mm |
| 110 | H | H | CO—4-Morpholinyl | H | H | 125–126 |
| 111 | H | $CH_3$ | $NO_2$ | H | H | 116–117 |
| 115 | H | $NH_2$ | H | H | H | 71–74 |
| 116 | H | $CO_2CH_2CH_3$ | H | H | H | 47–49 |
| 117 | H | H | $CO_2CH_3$ | H | H | 142–143 |
| 118 | H | H | $CO_2K$ | H | H | >250 |
| 119 | H | H | OH | H | H | 160–161 |

TABLE 1-continued

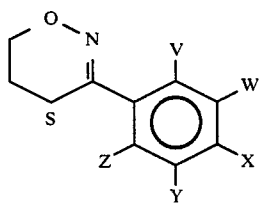

| COMPOUND | V | W | X | Y | Z | m.p. °C. or bp. |
|---|---|---|---|---|---|---|
| 125 | H | COOK | H | H | H | >250 |
| 126[1] | H | Cl | H | H | H | 51–54.5 |
| 127 | H | H | NO$_2$ | H | H | 168–170 |
| 130 | H | CN | H | H | H | 70–72 |
| 132 | F | H | H | H | H | 125/0.25 mm |
| 139[2] | Cl | H | H | H | H | oil |
| 140[3] | H | Cl | H | H | H | oil |

[1] Methyl group on 6- position of the 1,4,2-oxathiazine ring.
[2] Methyl group on 5- or 6- position of the 1,4,2-oxathiazine ring.
[3] Methyl group on 5- position of the 1,4,2-oxathiazine ring.

TABLE 2

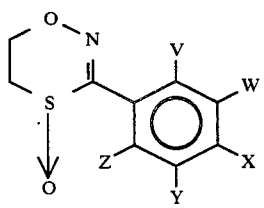

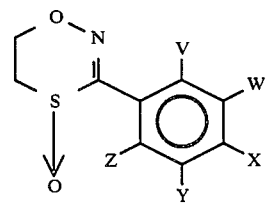

| COMPOUND | V | W | X | Y | Z | m.p. °C. |
|---|---|---|---|---|---|---|
| 5 | H | H | Cl | H | H | 72–75 |
| 15 | H | NO$_2$ | H | H | H | 149–153 |
| 19 | H | Cl | Cl | H | H | 104–7 |
| 28 | H | F | H | H | H | 78–81 |
| 29 | H | H | H | H | H | 68–70 |
| 32 | H | CH$_3$ | H | H | H | 68–69 |
| 36 | H | H | OCH$_3$ | H | H | 109–112 |
| 41 | H | OCH$_3$ | H | H | H | 62–64 |
| 42 | H | H | CH$_3$ | H | H | 100–102 |
| 46 | H | CF$_3$ | H | H | H | 89–90 |
| 52 | H | H | COCH$_3$ | H | H | 159–160 |
| 55 | Cl | H | H | H | Cl | 133–135 |
| 61 | H | H | OC$_6$H$_5$ | H | H | 155–157 |
| 67 | H | H | O(CH$_2$)$_3$CH$_3$ | H | H | 77–8 |
| 68 | H | Cl | H | Cl | H | 135–6 |
| 73 | H | H | (CH$_2$)$_3$CH$_3$ | H | H | 68 |
| 75 | H | H | C(CH$_3$)$_3$ | H | H | 101–3 |
| 76 | H | H | Br | H | H | 113–5 |
| 82 | H | H | CO$_2$CH$_2$CH$_3$ | H | H | 106–8 |
| 84 | H | Cl | H | H | H | 112–4 |
| 86 | H | H | CF$_3$ | H | H | 142–5 |
| 91 | H | CO$_2$CH$_3$ | H | H | H | 103–104 |
| 95 | H | H | C$_6$H$_5$ | H | H | 138–144 |
| 96 | H | Br | H | H | H | 104–106 |
| 102 | H | CONHC$_6$H$_5$ | H | H | H | 158–160 |
| 103 | H | H | SOCH$_3$ | H | H | 140–142 |
| 104 | H | H | SO$_2$CH$_3$ | H | H | 160–163 |
| 112 | H | H | CONHC$_6$H$_4$—2-CH$_3$ | H | H | 168–169 |
| 113 | H | H | OC$_5$H$_{11}$ | H | H | 68–70 |
| 120 | H | CH$_3$ | NO$_2$ | H | H | 156–158 |
| 121 | H | H | CO—morpholinyl | H | H | 182–183 |
| 122 | H | H | OCH$_2$CH$_3$ | H | H | 125–127 |
| 133 | H | CN | H | H | H | 153–155 |
| 134 | H | H | COOCH$_3$ | H | H | 137–138 |
| 135[1] | H | Cl | H | H | H | 95–99.5 |
| 136 | H | H | NO$_2$ | H | H | 190–193 |
| 140 | Cl | H | H | H | H | 94–95 |
| 141 | F | H | H | H | H | 102–104 |

[1] Methyl group on 6- position of the 1,4,2-oxathiazine ring.

TABLE 3

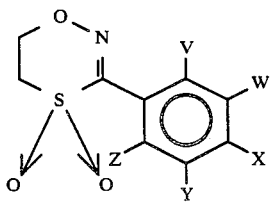

| COMPOUND | V | W | X | Y | Z | m.p. °C. |
|---|---|---|---|---|---|---|
| 4 | Cl | H | H | H | H | 125–127 |
| 7 | Cl | H | Cl | H | H | 101.5–102 |
| 17 | H | NO$_2$ | H | H | H | 135–140 |
| 20 | CH$_3$ | H | H | H | H | 118–120 |
| 25 | CH$_3$ | H | H | CH$_3$ | H | 85–86 |
| 43 | H | H | CH$_3$ | H | H | 131.5–132.5 |
| 49 | H | H | CN | H | H | 115–118 |

TABLE 3-continued

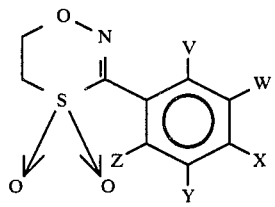

| COMPOUND | V | W | X | Y | Z | m.p. °C. |
|---|---|---|---|---|---|---|
| 53 | H | H | COCH$_3$ | H | H | 142–144 |
| 56 | Cl | H | H | H | Cl | 180–182 |
| 57 | H | H | H | H | H | 98–99 |
| 58 | H | Cl | Cl | H | H | 145–147 |
| 59 | H | H | Cl | H | H | 89–90 |
| 65 | H | Cl | H | Cl | H | 133–4 |
| 66 | H | H | O(CH$_2$)$_3$CH$_3$ | H | H | 104–5 |
| 72 | H | H | (CH$_2$)$_3$CH$_3$ | H | H | 88–90 |
| 74 | H | H | C(CH$_3$)$_3$ | H | H | 133–4 |
| 77 | H | H | Br | H | H | 147–8 |
| 81 | H | H | CO$_2$CH$_2$CH$_3$ | H | H | 118–20 |
| 83 | H | Cl | H | H | H | 102–4 |
| 85 | H | H | CF$_3$ | H | H | 158–9 |
| 90 | H | CO$_2$CH$_3$ | H | H | H | 101–102 |
| 94 | H | H | C$_6$H$_5$ | H | H | 142–145 |
| 97 | H | Br | H | H | H | 99–102 |
| 105 | H | H | CONHC$_6$H$_4$—2-CH$_3$ | H | H | 212–213 |
| 106 | H | CONHC$_6$H$_5$ | H | H | H | 162–163 |
| 114 | H | H | OC$_5$H$_{11}$ | H | H | 66–67 |
| 123 | H | H | CO-morpholinyl | H | H | 165–168 |
| 124 | H | H | OCH$_2$CH$_2$ | H | H | 123–124 |
| 128 | H | CH$_3$ | NO$_2$ | H | H | 140–141 |
| 129 | H | CF$_3$ | H | H | H | 104–104.5 |
| 137 | H | H | COOCH$_3$ | H | H | 173–176 |
| 138[1] | H | Cl | H | H | H | 123–126 |
| 142 | H | CN | H | H | H | 155–159 |
| 143 | F | H | H | H | H | 130–132 |

[1]Methyl group on 6- position of the 1,4,2-oxathiazine ring.

TABLE 4

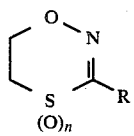

| COMPOUND | R | n | m.p. °C./bp. |
|---|---|---|---|
| 14 | 2-pyridinyl | 0 | 135–137 |
| 23 | 2-pyridinyl | 1 | 180 |
| 10 | 3-pyridinyl | 0 | 125–128 at 0.05 mm (6.67 Pa) |
| 24 | 3-pyridinyl | 1 | 46–51 |
| 21 | 4-pyridinyl | 1 | 150–158 |
| 22 | 4-pyridinyl | 2 | 185 |
| 33 | 2-furanyl | 1 | 77–78 |
| 44 | 2-furanyl | 2 | 92–93 |
| 37 | 2-thienyl | 0 | 86–89 |
| 38 | 2-thienyl | 1 | 107–109 |
| 40 | 2,4,5-trimethyl-3-furanyl | 0 | mp 35; bp 132/0.1 mm (13.3 Pa) |
| 11 | 4-pyridinyl | 0 | 80–82 |
| 31 | 2-furanyl | 0 | 128–129/1.3 mm |
| 131 | 4-ethyoxycarbonyl-3,5-dimethyl-2-furanyl | 0 | 66–7 |

All of the above compounds in Tables 1 to 4 were confirmed by elemental analysis and/or N.M.R. spectra and/or infrared spectra.

Compounds within the contemplation of this invention include the following (n being 0, 1 or 2):

| V | W | X | Y | Z | n |
|---|---|---|---|---|---|
| H | H | CONHC$_4$H$_9$ | H | H | 0 or 1 |
| H | H | CONHCH$_3$ | H | H | 0 or 1 |
| H | H | CN | H | H | 1 |
| H | Cl | Cl | H | H | 1 |
| H | Cl | H | H | H | 1[1] |

[1]Methyl group on 5- position of the 1,4,2-oxathiazine ring.

As indicated above, compounds of the invention are particularly useful in herbicidal, fungicidal, defoliant and desiccant applications, particularly in the form of an agricultural chemical formulation comprising an effective amount of the compound in admixture with a carrier therefor.

For herbicidal (post-emergent or pre-emergent) applications, a preferred class of compounds are those of the general formula given above, in which R$^1$ is hydrogen, C$_1$–C$_4$ linear or branched alkyl or bnezyl, n is 0, 1 or 2 and R has one of the following values:
phenyl or naphthyl;
phenyl substituted with 1 or 2 of the following groups:
halogen except 2-Cl if n is 2
C$_1$–C$_{12}$ alkyl
C$_5$–C$_6$ cycloalkyl
trihalomethyl
C$_1$–C$_8$ alkoxy (but not C$_4$–C$_8$ alkoxy if n is zero or 2)
phenoxy
tetrahydropyranyloxy
C$_1$–C$_8$ alkylthio $C_1$-$C_4$ alkylsulfinyl
$C_1$-$C_4$ alkylsulfonyl
$C_2$-$C_5$ alkylcarbonyl provided n is 0 or 1
carboxyl or its alkali metal salt
2- or 3-($C_2$-$C_5$ alkoxycarbonyl)
4-($C_2$-$C_5$ alkoxycarbonyl) provided n is 0 or 1
$C_2$-$C_5$ alkylaminocarbonyl
morpholinocarbonyl
amino
nitro
cyano
dioxolanyl;
4-pyridinyl if n is zero or 1;
thienyl provided n is not 2;
furanyl;
furanyl substituted with 1 to 3 of the following groups:
$C_1$-$C_4$ alkyl
$C_2$-$C_5$ alkoxycarbonyl.

More preferred herbicidal compounds are those wherein:
$R^1$ is hydrogen or $C_1$-$C_4$ linear or branched alkyl and if n is zero, 1 or 2,
R=phenyl substituted with 1 or 2 of the following groups:
3-$CF_3$
n-$C_1$-$C_4$ alkyl provided they are in 3- or 4-position;
3-pyridinyl;
furanyl;
furanyl substituted with 1 to 3 of the following groups:
methyl
$C_2$-$C_3$ alkoxycarbonyl.
if n is zero or 1,
R=phenyl;
phenyl substituted with 1 or 2 of the following groups:
F or Cl
trifluoromethyl;
thienyl;
if n is 1,
R=phenyl substituted with 1 or 2 of the following groups:
4-Br
4-$CF_3$
$C_1$-$C_5$ alkoxy
3-nitro
3-cyano.

Still more preferred herbicidal compounds are those wherein:
$R^1$ is hydrogen or methyl, and
if n is zero, 1 or 2,
R=phenyl substituted with 1 or 2 of the following groups:
4-Cl
3- or 4-(n-$C_1$-$C_3$ alkyl);
if n is 1 or 2,
R=2-furanyl;
if n is 1,
R=phenyl;
phenyl substituted with 1 or 2 of the following groups:
3-Cl or 3-F
4-trifluoromethyl
3-methoxy
3-nitro
4-($C_1$-$C_4$ alkyl);
2-thienyl;
if n is zero or 1,
R=3-pyridinyl;
if n is zero,
R=phenyl substituted with one of the following groups:
2,4-$Cl_2$
2-Cl
3-Cl
4-F
2-Cl-6-F.

For fungicidal applications, a preferred class of compounds are those of the formula given above, in which $R^1$ is hydrogen, $C_1$-$C_4$ linear or branched alkyl or benzyl, n is 0, 1 or 2, and R has one of the following values:
phenyl or naphthyl;
phenyl substituted with 1-2 of the following groups:
hydroxyl
halo
$C_1$-$C_{12}$ alkyl
$C_5$-$C_6$ cycloalkyl
trihalomethyl
phenyl
$C_1$-$C_5$ alkoxy or alkylthio
$C_2$-$C_5$ alkylcarbonyl
phenylcarbonyl
$C_1$-$C_4$ alkylsulfinyl
$C_1$-$C_4$ alkylsulfonyl
carboxy or its alkali metal salt
$C_2$-$C_5$ alkoxycarbonyl
$C_2$-$C_5$ alkylaminocarbonyl
phenylaminocarbonyl
tolylaminocarbonyl
morpholinocarbonyl, except when n is zero
amino
nitro
cyano
dioxolanyl;
pyridinyl, except 4-pyridinyl if n is zero;
thienyl provided n is not 2;
furanyl;
furanyl substituted with 1 to 3 of the following groups:
$C_1$-$C_4$ alkyl
$C_2$-$C_5$ alkoxycarbonyl.

More preferred fungicidal compounds are those wherein:
$R^1$ is hydrogen or $C_1$-$C_4$ linear or branched alkyl, and
if n is zero, 1 or 2,
R=phenyl or naphthyl;
phenyl substituted with 1 or 2 of the following groups:
F, Cl or Br in 3- or 4-positions;
if n is 1 or 2,
R=phenyl substituted with 1 or 2 of the following groups:
3- or 4-($C_1$-$C_4$ alkyl)
3- or 4-trifluoromethyl
$C_1$-$C_4$ alkoxy
phenoxy
$C_2$-$C_5$ alkylcarbonyl
$C_2$-$C_3$ alkoxycarbonyl
nitro
cyano;
if n is 1,
R=biphenylyl;

3-cyanophenyl;
4-pyridinyl;
thienyl.

Still more preferred fungicidal compounds are those in which, $R^1$ is hydrogen or methyl;
n is 1 or 2;
R is phenyl;
  phenyl substituted with 1-2 of the following groups:
    F or Cl
    methyl
    3-trifluoromethyl
    3-methoxy
    methylcarbonyl
    3-methoxycarbonyl
    4-methoxycarbonyl provided n is 1
    4-ethoxycarbonyl
    nitro;
  2-thienyl if n is 1;
  2-furanyl.

For desiccating plants, a preferred class of compounds are those in which $R^1$ is hydrogen, $C_1$-$C_4$ linear or branched alkyl or benzyl and
if n is zero, 1 or 2,
  R = phenyl or naphthyl;
  phenyl substituted with 1-2 of the following groups:
    Cl or Br in the 3-position
    $C_1$-$C_{12}$ alkyl in the 3- or 4 position
    3-trihalomethyl
    $C_1$-$C_3$ alkoxy or alkylthio
    $C_1$-$C_4$ alkylsulfinyl
    $C_1$-$C_4$ alkylsulfonyl
    carboxy or its alkali metal salt
    3-methoxycarbonyl
    4-ethoxycarbonyl
    amino
    cyano
    dioxolanyl;
  3-pyridinyl;
  4-nitrotolyl;
  furanyl;
  furanyl substituted with 1-3 of the following groups:
    $C_1$-$C_4$ alkyl
    $C_2$-$C_5$ alkoxycarbonyl;
if n is 1 or 2,
  R = phenyl substituted with:
    2-F or 4-Br
    4-trihalophenyl
    3-ethoxycarbonyl
    4-methoxycarbonyl
    4-nitro;
if n is zero or 1,
  R = phenyl substituted with
    2-Cl
    2-methyl
    2,5-$(CH_3)_2$
    $C_2$-$C_5$ alkylcarbonyl
    morpholinocarbonyl;
  4-pyridinyl;
  thienyl;
if n is zero,
  R = phenyl substituted with
    3-F
    2,6-$Cl_2$ or 2-Cl-6-F;

R = 2-pyridinyl.

More preferred compounds for desiccating plants are those in which $R^1$ is hydrogen or $C_1$-$C_4$ linear or branched alkyl and
if n is zero, 1 or 2,
  R = phenyl;
  phenyl substituted with
    3-(Cl or Br)
    3,4-$Cl_2$
    3-methoxy
    3-$CF_3$;
  3-pyridinyl;
  furanyl;
if n is zero or 1,
  R = phenyl substituted with:
    2-(Cl or F)
    3- or 4-(n-$C_1$-$C_4$ alkyl)
    2,5-$(CH_3)_2$
    3-trifluoromethyl
    3-methoxycarbonyl;
  4-pyridinyl;
  thienyl;
if n is zero,
  R = phenyl substituted with
    2-methyl;
if n is 1 or 2,
  R = phenyl substituted with
    4-$CF_3$;
if n is 1,
  R = 3-nitrophenyl.

For defoliating plants a preferred class of compounds are those in which $R^1$ is hydrogen, $C_1$-$C_4$ linear or branched alkyl or benzyl and
if n is zero, 1 or 2,
  R = phenyl;
  phenyl substituted with 1-2 groups:
    3- or 4-halo
    3,5-$Cl_2$
    2-($C_1$-$C_4$ alkyl)
    4-($C_3$-$C_4$ alkyl)
    2,5-$(CH_3)$
    phenyl
    3-methoxy
    4-($C_2$-$C_4$ alkoxy)
    $C_2$-$C_5$ alkoxycarbonyl
    3- or 4-carboxy, alkali metal salt
    4-methoxycarbonyl
    $C_2$-$C_5$ alkylaminocarbonyl
    phenylaminocarbonyl
    amino
    3-nitro
    3-cyano;
  3- or 4-pyridinyl;
  furanyl;
n is zero or 1,
  R = phenyl substituted with:
    2-halo
    2,4-dihalo
    2,5-$(CH_3)_2$
    4-$CF_3$
    4-pentyloxy
    3-($C_2$-$C_3$ alkoxycarbonyl)
    morpholinocarbonyl;
  thienyl;
n is 1 or 2,
  R = phenyl substituted with:
    3-$CF_3$ 4-methoxy
4-nitro
4-nitrotolyl
3,4-$Cl_2$;
n is zero,
R=phenyl
  phenyl substituted with:
    2-halo
    3-methyl
    3,5-$(CH_3)_2$
    phenoxy;
  furanyl substituted with methyl and ethoxycarbonyl;
n is 1,
R=phenyl substituted with:
    2,6-$Cl_2$
    4-$CH_3$
    4-ethoxycarbonyl;
n is zero or 2,
    phenyl substituted with tolylaminocarbonyl or 2-methyl.

More preferred compounds for defoliating plants are those in which $R^1$ is hydrogen or $C_1$-$C_4$ linear or branched alkyl and
if n is zero, 1 or 2,
R=phenyl substituted with:
    3-halo
    3,5-$Cl_2$
    3-methoxy
    4-carboxy alkali metal salt
    3-amino
    3-nitro
    3-cyano;
  3- or 4-pyridinyl;
if n is zero or 1,
R=phenyl substituted with:
    2-halo
    4-(Br or Cl)
    2,4-$Cl_2$
    2,5-$(CH_3)_2$;
  2-thienyl;
if n is zero, 1 or 2,
R=phenyl substituted with:
    3-$CF_3$
    3-$CH_3$-4-$NO_2$
    4-nitro
    4-methoxy;
if n is 0,
R=phenyl substituted with:
    phenoxy;
if n is 1,
R=phenyl substituted with:
    4-($C_1$-$C_4$ n-alkyl)
    $C_2$-$C_4$ alkoxy
    4-methylcarbonyl
    3-($C_2$-$C_3$ alkoxycarbonyl)
    4-methoxycarbonyl.

For herbicidal applications, compounds of this invention may be added as a "tank mix" to other herbicide solutions so that the number of different weed species controlled in a single application will be increased.

The procedures for using the present oxathiazine derivatives as herbicides may be in accordance with conventional agricultural practice. The chemicals are ordinarily applied as formulations containing a carrier and/or surface-active agent. The formulation may contain more than one of the described oxathiazine derivatives if desired; other active herbicides may be included in the formulation as well.

Thus, the chemical may be impregnated on finely divided or granular inorganic or organic carriers such as attapulgite clay, sand, vermiculite, ground corn cobs, activated carbon or other granular carriers known to the art. The impregnated granules may then be spread on the soil as preemergence herbicides. Furthermore, the chemical may be formulated as wettable powders by grinding them into a fine powder and mixing them with an inactive powdered carrier to which a surface active dispersing agent has been added. Typical powdered solid carriers are the various mineral silicates, e.g., mica, talc, pyrophyllite and clays. The wettable powder may then be dispersed in water and sprayed on the soil surface or weeds. Similarly, soluble or emulsifiable concentrate may be prepared by first dissolving the chemical in a solvent. The choice of solvent depends on the solubility of the particular chemical. Commonly used solvents are acetone, methyl ethyl ketone, $C_1$-$C_8$ alcohols such as methanol, ethanol, butanol, hexanol and 2-ethylhexanol; toluene, xylene, chloroform, furfuryl alcohol, phenol, naphtha, petroleum ether, kerosene or other aliphatic cycloaliphatic or aromatic solvents. Usually, a surface active agent or dispersant is added to the solvent. The resultant concentrate is then dispersed in water and applied by spraying. Suitable surface active agents and dispersants are well known to those skilled in the art and reference may be had to McCutcheon's Detergents and Emulsifiers, 1980, Allured Publishing Corp., Ridgewood, N.J.; or Hoffman et al. U.S. Pat. Nos. 2,614,916, cols. 2 to 4 and 2,547,724, cols. 3 and 4, for example of appropriate surface active agents. The concentration of active chemical in the formulation may vary widely, e.g., from 1 to 95%. For use as a preemergence herbicide, the chemical is applied to soil which contains weed and crop seed (either to the surface of the soil or incorporated into the upper 2.5 to 7.6 cm of soil).

The most suitable rate of application in any given case will depend on such factors as soil type, soil pH, soil organic matter content, the quantity and intensity of rainfall before and after treatment, the air and soil temperature, light intensity and light duration per day. All of these factors have an influence on the efficacy of the chemicals for use as herbicides.

EXAMPLE 18

To illustrate herbicide efficacy of the described 3-aryl-5,6-dihydro-1,4,2-oxathiazines, 600 mg chemical was dissolved in 10 ml organic solvent to which 30 mg conventional emulsifying agent (e.g., ethoxylated sorbitan monolaurate "Tween 20" [trademark]) was added; in most cases acetone was used as the solvent. The solution was diluted to 100 ml with distilled water. Twenty milliliters of this 6000 ppm solution was diluted to 250 ppm with distilled water. The chemical was applied at the rate of 11.2 kg/ha (kilograms per hectare) by drenching 46 ml of the 250 ppm solution on the surface of soil in 11.4 cm diameter plastic pots which had been sown with the following weed seeds: velvetleaf (*Abutilon theophrasti* Medic.) or rough pigweed (*Amaranthus retroflexus* L.), jimsonweed (*Datura stramonium* L.), tall morningglory (*Ipomea purpurea* (L.) Roth), crabgrass (*Digitaria ischaemum* (Schreb.) Muhl) or switchgrass (*Panicum virgatum* L.), barnyardgrass (*Echinochloa crusgalli* (L.) Beauv.) and giant foxtail (*Setaria faberi* Herrm.) or green foxtail (*Setaria viridis*

(L.) Beauv.). The percent control of the weeds compared to untreated checks was determined two weeks after treatment. TABLE 5 shows the results with the preemergence herbicides of the invention prepared in accordance with the above examples.

EXAMPLE 19

To illustrate effectiveness of the described oxathiazines as postemergence herbicides the 6000 ppm solutions described under Example 18 were atomized with a number 152 DeVilbiss (trademark) sprayer, wetting the foliage to the drip point. The weeds, which are the same species as described under Example 18, were treated six days after emergence. The percent control was evaluated two weeks after treatment. TABLE 6 shows the results with postemergence herbicides of the invention.

TABLE 5

PREEMERGENCE HERBICIDE ACTIVITIES OF OXATHIAZINES AT 11.2 kg/ha
PERCENT WEED CONTROL

| COMPOUND | PIGWEED OR VELVETLEAF* | JIMSON WEED | MORNING GLORY | BARNYARD GRASS | CRABGRASS OR SWITCH-GRASS** | GIANT OR GREEN*** FOXTAIL |
|---|---|---|---|---|---|---|
| 5 | 98 | 0 | 0 | 10 | 0 | 25 |
| 9 | 90 | 0 | 0 | 25 | 0 | 0 |
| 10 | 90 | 75 | 0 | 50 | 25 | 0 |
| 13 | 100 | 0 | 10 | 15 | 0 | 0 |
| 18 | 100 | 0 | 0 | 0 | 0 | 0 |
| 27 | 85 | 0 | 0 | 0 | 0 | 0 |
| 28 | 100 | 0 | 35 | 30 | 95 | 98*** |
| 29 | 100 | 0 | 0 | 30 | 95 | 95*** |
| 30 | 100 | 0 | 0 | 20 | 80 | 80*** |
| 32 | 100 | 0 | 0 | 50 | 25 | 0*** |
| 33 | 95 | 98 | 0 | 50 | 0 | 25*** |
| 36 | 100 | 0 | 0 | 15 | 0 | 0*** |
| 37 | 100 | 0 | 0 | 0 | 0 | 0*** |
| 38 | 100 | 0 | 0 | 35 | 30 | 30*** |
| 39 | 100 | 0 | 100 | 0 | 0 | 0*** |
| 41 | 100 | 0 | 0 | 0 | 75 | 0*** |
| 42 | 100 | 0 | 0 | 50 | 75 | 75*** |
| 43 | 40 | 0 | 0 | 0 | 0 | 0*** |
| 44 | 70 | 0 | 0 | 30 | 80 | 65*** |
| 46 | 100 | 0 | 0 | 0 | 0 | 0*** |
| 47 | — | 95 | 0 | 0 | 100 | 100*** |
| 54 | — | 0 | 0 | 80 | 90** | 100*** |
| 55 | — | 100 | 0 | 90 | 95** | 75*** |
| 56 | — | 100 | 0 | 50 | 80** | 25*** |
| 67 | 0* | 0 | 0 | 40 | 20** | 80*** |
| 68 | 0* | 0 | 0 | 25 | 50** | 95*** |
| 73 | 0* | 0 | 0 | 50 | 95** | 50*** |
| 75 | 0* | 0 | 0 | 60 | 95** | 95*** |
| 76 | 0* | 0 | 0 | 50 | 90** | 95*** |
| 78 | 0* | 0 | 0 | 0 | 30** | 50*** |
| 84 | 0* | 70 | 0 | 30 | 50** | 0*** |
| 86 | 0* | 75 | 0 | 75 | 95** | 95*** |
| 122 | 0* | 0 | 0 | 50 | 15** | 60*** |
| 129 | 100* | 0 | 0 | 0 | 0** | 90*** |
| 133 | 0 | 0 | 0 | 50 | 30** | 50*** |
| 135 | 0* | 0 | 0 | 75 | 90** | 80*** |

TABLE 6

POSTEMERGENCE HERBICIDE ACTIVITY OF OXATHIAZINES AT 6000 PPM
PERCENT WEED CONTROL

| COMPOUND | PIGWEED OR VELVETLEAF* | JIMSON WEED | MORNING GLORY | BARNYARD GRASS | CRABGRASS OR SWITCH-GRASS** | GIANT OR GREEN*** FOXTAIL |
|---|---|---|---|---|---|---|
| 1 | 100 | 90 | 5 | 95 | 100 | 100 |
| 3 | 100 | 35 | 65 | 100 | 85 | 100 |
| 5 | 100 | 100 | 100 | 100 | 100 | 100 |
| 6 | 100 | 100 | 30 | 100 | 100 | 100 |
| 7 | 0 | 0 | 5 | 10 | 5 | 5 |
| 8 | 100 | 100 | 90 | 100 | 100 | 100 |
| 9 | 100 | 10 | 98 | 100 | 100 | 100 |
| 10 | 100 | 0 | 20 | 95 | 95 | 95 |
| 11 | 100 | 5 | 35 | 35 | 50 | 75 |
| 12 | 50 | 0 | 10 | 25 | 10 | 0 |
| 13 | 100 | 0 | 10 | 15 | 0 | 0 |
| 15 | 100 | 50 | 98 | 95 | 80 | 30 |
| 16 | 20 | 5 | 10 | 20 | 25 | 15 |
| 17 | 25 | 5 | 10 | 10 | 5 | 5 |
| 18 | 100 | 20 | 45 | 90 | 75 | 50 |
| 19 | 65 | 10 | 35 | 60 | 20 | 10 |
| 20 | 0 | 0 | 0 | 10 | 0 | 0 |
| 21 | 100 | 5 | 25 | 60 | 95 | 50 |
| 24 | 100 | 100 | 100 | 95 | 75 | 45 |

TABLE 6-continued

POSTEMERGENCE HERBICIDE ACTIVITY OF OXATHIAZINES AT 6000 PPM

PERCENT WEED CONTROL

| COMPOUND | PIGWEED OR VELVETLEAF* | JIMSON WEED | MORNING GLORY | BARNYARD GRASS | CRABGRASS OR SWITCH-GRASS** | GIANT OR GREEN*** FOXTAIL |
|---|---|---|---|---|---|---|
| 25 | 5 | 5 | 5 | 25 | 10 | 10 |
| 26 | 100 | 100 | 70 | 98 | 98 | 95 |
| 27 | 100 | 5 | 15 | 98 | 100 | 98 |
| 28 | 100 | 100 | 100 | 100 | 100 | 100*** |
| 29 | 100 | 100 | 100 | 100 | 100 | 100*** |
| 30 | 100 | 5 | 50 | 100 | 100 | 100*** |
| 31 | 100 | 10 | 30 | 95 | 100 | 100*** |
| 32 | 100 | 100 | 100 | 100 | 100 | 100*** |
| 33 | 100 | 100 | 100 | 95 | 100 | 100*** |
| 34 | 100 | 0 | 5 | 90 | 75 | 90*** |
| 35 | 100 | 10 | 85 | 70 | 50 | 50*** |
| 36 | 100 | 0 | 5 | 70 | 95 | 95*** |
| 37 | 100 | 0 | 0 | 55 | 25 | 25*** |
| 38 | 100 | 90 | 75 | 80 | 80 | 90*** |
| 39 | 100 | 20 | 25 | 100 | 100 | 100*** |
| 40 | 100 | 25 | 90 | 90 | 30 | 30*** |
| 41 | 100 | 80 | 100 | 95 | 90 | 90*** |
| 42 | 100 | 100 | 100 | 100 | 70 | 85*** |
| 43 | 90 | 80 | 70 | 90 | 75 | 90*** |
| 44 | 90 | 80 | 100 | 95 | 75 | 90*** |
| 45 | 100 | 20 | 30 | 90 | 95 | 100*** |
| 46 | 80 | 65 | 75 | 60 | 40 | 25*** |
| 47 | 100 | 10 | 45 | 75 | 75 | 90*** |
| 48 | 100 | 0 | 5 | 80 | 75 | 100*** |
| 49 | 95 | 0 | 10 | 25 | 10 | 35*** |
| 50 | 50 | 0 | 5 | 5 | — | 5*** |
| 51 | 100 | 0 | 5 | 5 | — | 15*** |
| 52 | 100 | 0 | 30 | 25 | — | 50*** |
| 54 | — | 50 | 5 | 100 | 100** | 100*** |
| 57 | 25 | 0 | 45 | 55 | — | 90*** |
| 58 | 100 | — | 85 | 50 | 25** | 80*** |
| 59 | 60 | 90 | 100 | 95 | 65** | 95*** |
| 60 | 0 | 0 | 0 | 20 | 0** | 20*** |
| 61 | — | 0 | 0 | 45 | — | 20*** |
| 64 | 0* | 0 | 0 | 5 | 0** | 10*** |
| 65 | 0* | 0 | 0 | 10 | 0** | 10*** |
| 67 | 0* | 0 | 5 | 45 | 5** | 35*** |
| 68 | 0* | 0 | 25 | 70 | 20** | 80*** |
| 69 | 0* | 0 | 0 | 5 | 0** | 10*** |
| 70 | 0* | 0 | 25 | 95 | 0** | 95*** |
| 71 | 100* | 0 | 20 | 100 | 0** | 95*** |
| 72 | 25* | 0 | 55 | 75 | 0** | 40*** |
| 73 | 100* | 100 | 100 | 100 | 10** | 95*** |
| 74 | 0* | 0 | 0 | 15 | 0** | 10*** |
| 75 | 10* | 0 | 10 | 80 | 0** | 65*** |
| 76 | 5* | 0 | 25 | 50 | 0** | 45*** |
| 77 | 0* | 0 | 20 | 30 | 5** | 10*** |
| 78 | 0* | 0 | 50 | 80 | 30** | 90*** |
| 79 | 0* | 0 | 0 | 10 | — | — |
| 80 | 0* | 0 | 5 | 75 | — | — |
| 81 | 0* | 0 | 5 | 0 | — | — |
| 82 | 25* | 25 | 75 | 80 | — | — |
| 83 | 65* | 25 | 75 | 95 | — | — |
| 84 | 50* | 25 | 60 | 100 | — | — |
| 85 | 0* | 0 | 35 | 90 | — | — |
| 86 | 75* | 20 | 75 | 100 | — | — |
| 87 | 100* | 0 | 30 | 95 | — | — |
| 89 | 40* | 0 | 0 | 35 | 0** | 75*** |
| 90 | 0* | 0 | 75 | 80 | 90** | 100*** |
| 91 | 15* | 0 | 85 | 65 | 5** | 25*** |
| 92 | 100* | 90 | 85 | 100 | 100** | 100*** |
| 93 | 0* | 0 | 5 | 15 | 0** | 25*** |
| 96 | 5* | 0 | 20 | 70 | 0** | 30*** |
| 97 | 5* | 0 | 20 | 55 | 5** | 40*** |
| 98 | 0* | 0 | 0 | 20 | 0** | 25*** |
| 99 | 0* | 0 | 5 | 0 | 0** | 0** |
| 101 | 10* | 0 | 20 | 15 | 0** | 15*** |
| 102 | 0* | 0 | 5 | 0 | 0** | 0*** |
| 103 | 5* | 0 | 15 | 30 | 0** | 25*** |
| 107 | 0* | 0 | 5 | 15 | 0** | 10*** |
| 108 | 15* | 0 | 40 | 60 | 5** | 55*** |
| 109 | 0* | 0 | 0 | 0 | 0** | 5*** |
| 110 | 15* | 0 | 25 | 65 | 5** | 100*** |
| 111 | 0* | 0 | 0 | 0 | 0** | 5*** |
| 112 | 0* | 0 | 5 | 10 | 0** | 10*** |

TABLE 6-continued

POSTEMERGENCE HERBICIDE ACTIVITY
OF OXATHIAZINES AT 6000 PPM

PERCENT WEED CONTROL

| COMPOUND | PIGWEED OR VELVETLEAF* | JIMSON WEED | MORNING GLORY | BARNYARD GRASS | CRABGRASS OR SWITCH-GRASS** | GIANT OR GREEN*** FOXTAIL |
|---|---|---|---|---|---|---|
| 113 | 100* | 0 | 100 | 100 | 10** | 100*** |
| 114 | 0* | 0 | 10 | 70 | 0** | 100*** |
| 115 | 0* | 0 | 0 | 10 | 0** | 60*** |
| 116 | 0* | 0 | 5 | 40 | 15** | 75*** |
| 117 | 0* | 0 | 0 | 5 | 0** | 15*** |
| 118 | 0* | 0 | 0 | 40 | 0** | 85*** |
| 120 | 20* | 15 | 45 | 5 | 0** | 35*** |
| 121 | 5* | 5 | 10 | 45 | 0** | 55*** |
| 122 | 10* | 50 | 80 | 90 | 0** | 100*** |
| 123 | 0* | 0 | 5 | 35 | 0** | 45*** |
| 124 | 0* | 0 | 5 | 25 | 0** | 75*** |
| 125 | 15* | 0 | 5 | 45 | 0** | 35*** |
| 126 | 95* | 5 | 35 | 25 | 55** | 85*** |
| 127 | 0* | 0 | 15 | 0 | — | — |
| 129 | 50* | 0 | 30 | 90 | 95** | 75*** |
| 130 | 90* | 0 | 20 | 95 | 5** | 75*** |
| 132 | 100* | 0 | 50 | 100 | 20** | 70*** |
| 133 | 0* | 0 | 20 | 80 | 5** | 50*** |
| 134 | 0* | 0 | 30 | 75 | 0** | 10*** |
| 135 | 100* | 0 | 15 | 95 | 85** | 95*** |
| 136 | 100* | 85 | 100 | 100 | 70** | 80*** |
| 138 | 0* | 0 | 0 | 10 | 9** | 0*** |

Procedures for using the compounds of this invention as plant desiccants and defoliants may be in accordance with the state of the art in conventional agricultural practice. The active ingredient(s) may be included in one or more formulations suitable for use in conventional application equipment. Such formulations may be of several different physical and chemical types, any of which could be made by anyone familiar with the art. For instance, the active ingredient(s) may be formulated into a soluble or emulsifiable concentrate that is prepared by dissolving the active ingredient(s) in one or more suitable solvents, such as acetone, toluene, or other aliphatic or aromatic hydrocarbons, to which a dispersing agent has been added. Alternatively, the active ingredient(s) may be formulated as a wettable powder by grinding it into a fine powder and mixing it with an inactive powdered carrier, to which a dispersing agent has been added. Typical inactive powdered carriers include attapulgite clay, vermiculite, talc, corn cob, activated carbon, mica and pyrophyllite. Alternatively, a wettable powder may be formulated by spraying a solution of the active ingredient(s) in organic solvent onto the surface of an active powdered carrier as it is blended. The solvent is subsequently allowed to vaporize. The concentration of the active ingredient(s) in formulations of all types may vary widely, ranging from 0.1 to 95% active ingredient by weight.

Formulations bearing the active ingredient(s) may be dispersed in water and applied to target plants. Surface active agents may be added to the applied solution to increase its qualitative or quantitive range of activity. Suitable surface active agents are well known to those skilled in the art. Reference may be made to McCutcheon's Detergents and Emulsifiers (1980, Allured Publ. Co., Ridgewood, NJ) or to Hoffman et al in U.S. Pat. Nos. 2,614,916 (cols. 2 to 4) and 2,574,724 (cols. 3 and 4) for examples of appropriate surface active agents.

The most suitable dosage of application of the active ingredient(s) and the type and amount of adjuvant substances to be added to the spray solution will depend on a number of factors, including the specific biological effect desired; the air and soil temperature; the quantity and intensity of rainfall before and after treatment; the soil type, pH, fertility and moisture content; the physiological condition and vigor of the target plants; the relative humidity and wind velocity of the air around the crop; the extent and density of the foliar canopy of the target plant; the light quality, intensity and duration each day; and the type and interval of previous and subsequent crop protectant chemical applications. All of these factors may have an influence on the efficacy of chemicals applied as harvest aids.

EXAMPLE 20

To illustrate the effectiveness of the described oxathiazines as crop plant desiccants, a 6000 ppm solution/suspension of active ingredient was made up as described in Example 18. The chemical solutions/suspensions were applied to soybean[1] and cotton[2] plants as in Example 19. After 3 weeks in the greenhouse, the plants were scored for leaf desiccation on a 0 to 100 scale, 0 being no damage and 100 being complete kill. A rating system suggested by Frans and Talbert (1977. Research Methods in Weed Science, 2nd edition, Southern Weed Science Society) was used as a guide. The data obtained appear in Table 7.

(1)*Glycine max* (L.) Merr. cv. Williams
(2)*Gossypium hirsutum* (L.) cv. Stoneville 213

TABLE 7

FOLIAGE DESICCATION ON COTTON AND SOYBEAN AT 6000 PPM

| | % desiccation | |
|---|---|---|
| Compound No. | soybean | cotton |
| 1 | 5 | 35 |
| 3 | 100 | 100 |
| 5 | 100 | 100 |
| 6 | 95 | 100 |
| 7 | 40 | 0 |
| 8 | 100 | 100 |
| 9 | 100 | 100 |
| 10 | 98 | 98 |
| 11 | 100 | 100 |
| 12 | 5 | 50 |
| 13 | 0 | 100 |
| 14 | 35 | 0 |

TABLE 7-continued
FOLIAGE DESICCATION ON COTTON AND SOYBEAN AT 6000 PPM

| Compound No. | % desiccation soybean | % desiccation cotton |
|---|---|---|
| 15 | 85 | 95 |
| 16 | 98 | 100 |
| 17 | 40 | 15 |
| 18 | 98 | 98 |
| 19 | 95 | 100 |
| 21 | 100 | 98 |
| 24 | 100 | 100 |
| 26 | 100 | 100 |
| 27 | 100 | 100 |
| 28 | 100 | 100 |
| 29 | 100 | 100 |
| 30 | 100 | 100 |
| 31 | 100 | 50 |
| 32 | 100 | 100 |
| 33 | 100 | 100 |
| 34 | 65 | 30 |
| 35 | 100 | 95 |
| 36 | 100 | 40 |
| 37 | 95 | 35 |
| 38 | 100 | 85 |
| 39 | 100 | 100 |
| 40 | 90 | 25 |
| 41 | 100 | 100 |
| 42 | 100 | 95 |
| 43 | 85 | 20 |
| 44 | 90 | 100 |
| 45 | 75 | 60 |
| 46 | 95 | 100 |
| 47 | 90 | 85 |
| 48 | 30 | 15 |
| 49 | 30 | 20 |
| 50 | 50 | 20 |
| 51 | 15 | 80 |
| 52 | 80 | 30 |
| 54 | 30 | 10 |
| 57 | 90 | 5 |
| 58 | 95 | 100 |
| 59 | 95 | 0 |
| 60 | 35 | 0 |
| 61 | 80 | 0 |
| 64 | 25 | 0 |
| 65 | 25 | 0 |
| 57 | 90 | 5 |
| 68 | 95 | 100 |
| 69 | 45 | 0 |
| 71 | 95 | 95 |
| 72 | 85 | 25 |
| 73 | 100 | 95 |
| 74 | 30 | 0 |
| 75 | 90 | 0 |
| 76 | 55 | 90 |
| 77 | 65 | 0 |
| 79 | 65 | 5 |
| 80 | 85 | 5 |
| 81 | 65 | 0 |
| 82 | 100 | 30 |
| 83 | 100 | 90 |
| 84 | 95 | 100 |
| 85 | 80 | 15 |
| 86 | 100 | 65 |
| 87 | 95 | 10 |
| 89 | 95 | 100 |
| 90 | 90 | 5 |
| 91 | 95 | 100 |
| 92 | 95 | 100 |
| 93 | 70 | 10 |
| 96 | 95 | 100 |
| 97 | 95 | 100 |
| 98 | 25 | 0 |
| 101 | 75 | 30 |
| 103 | 70 | 20 |
| 104 | 25 | 15 |
| 108 | 55 | 10 |
| 110 | 65 | 5 |
| 111 | 55 | 0 |
| 113 | 95 | 90 |
| 114 | 30 | 0 |
| 116 | 60 | 0 |
| 118 | 20 | 0 |
| 120 | 0 | 65 |
| 121 | 35 | 5 |
| 122 | 80 | 20 |
| 124 | 25 | 0 |
| 125 | 20 | 5 |
| 126 | 85 | 100 |
| 128 | 0 | 25 |
| 129 | 85 | 100 |
| 130 | 100 | 100 |
| 131 | 55 | 0 |
| 132 | 95 | 100 |
| 133 | 95 | 100 |
| 134 | 85 | 10 |
| 135 | 95 | 100 |
| 136 | 95 | 100 |
| 137 | 35 | 0 |
| 138 | 30 | 100 |

EXAMPLE 21

To further illustrate the effectiveness of the described 3-aryl-5,6-dihydro-1,4,2-oxathiazines as plant defoliants, a 6000 ppm weight for volume (w/v) solution/suspension of tested chemical was prepared by dissolving 600 mg chemical in 10 ml suitable organic solvent. The solution was diluted to 100 ml with distilled water containing about 2000 ppm w/v surface active agent (e.g., "Tween 20"). Twenty-five (25) ml of this 6000 ppm solution/suspension were diluted to 100 ml with distilled water containing about 2000 ppm surface active agent, resulting in a 1500 ppm solution/suspension of test chemical. The chemical was applied to cotton plants (*Gossypium hirsutum* L. "Stoneville 213") by immersion of the lower leaves. At the time of treatment, the cotton plants had 2 to 4 true leaves. After treatment, the plants were returned to the greenhouse for about two weeks, at which time the plants were evaluated for defoliation of the treated leaves. The scoring system used: 1=5-25% defoliation, 2=26-50%, 3=51-70%, 4=71-85%, 5=86-100%. The results appear in TABLE 8.

TABLE 8
COTTON DEFOLIATION AT 1500 PPM

| Compound No. | Defoliation Score |
|---|---|
| 1 | 5 |
| 3 | 5 |
| 5 | 5 |
| 6 | 5 |
| 9 | 5 |
| 10 | 5 |
| 11 | 5 |
| 12 | 5 |
| 15 | 5 |
| 16 | 2 |
| 17 | 5 |
| 18 | 5 |
| 20 | 5 |
| 23 | 2 |
| 24 | 5 |
| 26 | 5 |
| 27 | 5 |
| 28 | 5 |
| 31 | 1 |
| 33 | 3 |
| 35 | 5 |
| 36 | 5 |
| 37 | 4 |

TABLE 8-continued
COTTON DEFOLIATION AT 1500 PPM

| Compound No. | Defoliation Score |
|---|---|
| 38 | 5 |
| 39 | 2 |
| 41 | 5 |
| 42 | 2 |
| 44 | 3 |
| 46 | 5 |
| 51 | 3 |
| 52 | 5 |
| 55 | 1 |
| 60 | 5 |
| 63 | 3 |
| 64 | 5 |
| 65 | 5 |
| 66 | 1 |
| 67 | 4 |
| 68 | 5 |
| 69 | 1 |
| 70 | 1 |
| 71 | 2 |
| 72 | 3 |
| 73 | 4 |
| 74 | 1 |
| 75 | 2 |
| 76 | 5 |
| 77 | 2 |
| 78 | 1 |
| 82 | 2 |
| 83 | 2 |
| 84 | 5 |
| 86 | 1 |
| 87 | 1 |
| 88 | 1 |
| 89 | 5 |
| 91 | 5 |
| 92 | 5 |
| 94 | 1 |
| 95 | 2 |
| 96 | 5 |
| 97 | 5 |
| 100 | 1 |
| 105 | 1 |
| 106 | 1 |
| 108 | 1 |
| 109 | 1 |
| 110 | 1 |
| 113 | 1 |
| 114 | 1 |
| 115 | 4 |
| 116 | 4 |
| 117 | 2 |
| 118 | 5 |
| 120 | 5 |
| 121 | 2 |
| 122 | 5 |
| 124 | 2 |
| 125 | 1 |
| 126 | 5 |
| 128 | 5 |
| 129 | 5 |
| 130 | 5 |
| 131 | 2 |
| 132 | 5 |
| 133 | 5 |
| 134 | 5 |
| 136 | 5 |
| 135 | 5 |
| 137 | 2 |
| 138 | 5 |

Similar defoliating activity is observed with compounds of this invention wherein R is trichlorophenyl, $R^1$ is n-butyl, t-butyl or benzyl and n is 0, 1 or 2.

In fungicidal applications, the chemicals may be applied directly to plants (i.e. seeds, foliage) or to soil in which plants are growing or to be grown, to protect against the harmful effects of pathogenic fungi. For example, the chemical may be applied to seeds by tumbling the chemical with the seeds, either alone or in admixture with a powdered solid carrier. Typical powdered solid carriers are the various mineral silicates, e.g., mica, talc, pyrophyllite, and clays. The chemical may also be applied to the seeds in admixture with a conventional surface-active wetting agent, with or without additional powdered solid carrier, as by first wetting the mixture with a small amount of water and then tumbling the seeds in the slurry. The surface-active wetting agents that may be used with the fungicide may be any of the conventional anionic, non-ionic, or cationic surface-active agents. Such surface-active agents are well known and reference is made to U.S. Pat. No. 2,546,724, columns 3 and 4, for detailed examples of the same. As a seed protectant, the amount of the chemical coated on the seeds will be ¼ to 12 oz. (7–350 g) per hundred lbs. (45.5 kg) of the seed. As a soil treatment for fungi, the chemical may be applied: (a) as a dust in admixture with sand or soil a powdered solid carrier such as a mineral silicate, with or without an additional surface-active wetting agent, to the furrows simultaneously with the planting of the seeds; or (b) an aqueous spray, if desired including a surface-active or dispersing agent, or a surface-active or dispersing agent and a powdered solid carrier, to the seed rows before, or with, or after planting the seeds. As a soil treatment, the amount of the chemical applied to the seed rows will be from 0.1 to 10 pounds per acre (0.112 to 11.2 kg/ha) based on rows 2" (5 cm) wide and 2" (5 cm) deep a distance of 40" (102 cm) apart. Also, as a soil treatment, the chemical may be applied broadcast using a similar dust or aqueous spray with an application rate of 1.0 to 100 pounds per acre (1.12 to 112 kg/ha). As a foliage treatment, the chemical may be applied to growing plants at a rate of ¼ to 10 pounds per acre (0.28 to 11.2 kg/ha). Such application is generally as an aqueous spray which also contains a surface-active or dispersing agent, with or without a powdered solid carrier or hydrocarbon solvent. These sprays usually are repeated at time intervals ranging from three days to two weeks during the growing season. Typical formulations are as follows (all percentages are by weight):

(a) Emulsifiable concentrate:

| | |
|---|---|
| 48.1% | Active Ingredient |
| 11.1% | Surfactant (e.g., polyoxyethylene sorbitan monooleate) |
| 40.8% | Xylene |
| 100.0% | Total |

(b) Wettable powder:

| | |
|---|---|
| 75.0% | Active Ingredient |
| 2.0% | Triton (trademark) X-120 |
| 2.0% | Daxad (trademark) - 11 |
| 21.0% | Dixie clay |
| 100.0% | Total |

Triton X-120 is an alkylaryl polyether alcohol (9–10 moles polyethylene oxide) in dry powdered form (40% active on an insoluble carrier). The active ingredient in Triton X-120 is Triton X-100, which is a liquid nonionic surfactant (isooctyl-phenylpolyethoxyethanol, obtained by condensing the alkylphenylphenol with ethylene oxide). Daxad-11 is polymerized sodium salt of alkylnaphthalene sulfonic acid (more particularly, the sodium salts of binaphthyl/methane sulfonic acids obtained from naphthalene, sulfuric acid and formaldehyde, according to U.S. Pat. No. 1,336,759, Schmidt, Apr. 13, 1920).

EXAMPLE 22

Foliage Spray Treatment for Control of Established Bean Rust disease caused by the fungus (*Uromyces phaseoli*)

Although many chemicals will serve to protect plants from disease, it is often desirable to draw upon chemicals which have therapeutic properties to arrest the development of disease that has already become established. This example illustrates such properties.

Two hundred (200) milligrams of chemical were dissolved in 20 ml of acetone and 60 mg of a surfactant such as Triton X-100. This preparation was diluted with 80 ml distilled water giving a chemical suspension of 2000 ppm. Further serial dilutions were prepared from this as desired. The chemical suspensions were sprayed on duplicate pots, each containing two snapbean plants which had, 48 hours prior to this, been inoculated with the bean rust fungus *Uromyces phaseoli typica* Arth. At the time of the chemical spray the bean plants had just begun to expand their first trifoliolate leaves. The test plants were then placed in a chamber for 24 hours at 75° F. (24° C.) and 100% relative humidity. After this time the plants were returned to the greenhouse. About 10 days later the plants were scored for disease control, with the results shown in TABLE 9.

TABLE 9

Bean Rust Disease Control by Foliar Application at 1000 ppm

| COMPOUND | % DISEASE CONTROL |
|---|---|
| 29 | 95 |
| 28 | 90* |
| 5 | 95 |

*Some plant injury at this dosage.

EXAMPLE 23

Foliar Spray for Protecting Tomato Plants from infection by the Early Blight Fungus, *Alternaria solani*

Test procedure:

One gram of the chemical to be tested was ground with three ml of acetone and 50 mg of a non-ionic surface-active agent (Triton X-100). The acetone and surface-active agent are known to be inactive in this biological test. The mixture was diluted with water, giving suspensions containing 500 and 2000 ppm of the chemical. These suspensions were sprayed on duplicate six-inch (ca. 15 cm) tomato plants (variety Clark's Early Special) using a gun-type sprayer. Twenty-four hours later the treated and untreated check plants were inoculated with a suspension of *Alternaria solani* spores by means of a 20 second spray from an atomizer sprayer (delivery rate 1 ml per second). The plants were then kept overnight in a controlled chamber at a temperature of 75° F. (24° C.) and 100% relative humidity. In the morning the plants were transferred to the greenhouse. Three days later the disease was scored by comparing the number of disease lesions of the treated plants with the untreated control. The formula used to determine percent control is:

$$100 - \frac{\text{(Avg. no. lesions on treated plant)}}{\text{(Avg. no. lesions on untreated plant)}} \times$$

100 = percent control

The results are shown in TABLE 10.

TABLE 10

Control of Tomato Early Blight Disease by Foliar Application at 1000 ppm.

| COMPOUND | % DISEASE CONTROL |
|---|---|
| 4 | 92 |

EXAMPLE 24

Foliar Spray for protecting plants from infection by the Rice Blast fungus, *Piricularia oryza*.

Test procedure:

The chemical suspensions were prepared in manner described in Example 23. The suspensions were sprayed on duplicate pots of clustered 7-day old barley plants (variety Herta) using a gun-type sprayer. The plants were then placed in a greenhouse together with untreated check plants and allowed to dry. All test plants were inoculated with the fungus by spraying with a suspension of *Piricularia oryzae* spores (20,000–40,000 spores/ml) to which a standard wetting agent has been added (Tween 20, 6 drops/300 ml). After inoculation the plants were kept in a temperature-humidity control chamber for 24–48 hours at 70° F. (21° C.) to allow infection. Plants were then removed and placed in a 70° F. (21° C.) greenhouse to allow disease development. After 5 to 7 days, blast lesions appeared on the leaves. Disease control was evaluated by either counting lesions if infection was moderate or evaluating by a disease rating scale of 0–6 with 6 being severe disease. Percent control was computed by comparing the treatment scores with that of the untreated control (TABLE 11).

TABLE 11

Control of Piricularia Blast Disease On Barley by Foliar Application

| COMPOUND | PPM | % DISEASE CONTROL |
|---|---|---|
| 32 | 1000 | 87 |
| 4 | 500 | 84 |
| 21 | 1000 | 83 |
| 65 | 500 | 85 |
| 77 | 500 | 85 |
| 91 | 500 | 100 |

EXAMPLE 25

Antifungal activity as demonstrated by laboratory tests on fungus cultures.

The chemicals of the invention were dissolved in acetone, and applied at 500 ppm to 13 mm antibiotic testing discs by dipping the discs in the test solutions. After drying, the treated discs were placed on an agar plate (4 per plate), then 7 mm plugs of mycelium of various fungi were placed on the center of the discs in such fashion that the fungus mat was in direct contact with the treated disc. The fungitoxic activity of the chemicals was measured by comparing growth (colony radius) of the fungus on the treated discs with that on untreated controls. Colony radius was measured when untreated controls reached 80–90% of the area available for growth on the plates. The fungi tested were *Alternaria solani* (A), *Fusarium oxysporum* (F), Pythium sp. (P)

and *Sclerotium rolfsii* (S). The results are shown in TABLE 12.

TABLE 12

| COMPOUND | % INHIBITION @ 500 ppm | | | |
|---|---|---|---|---|
| | A | F | P | S |
| 6 | 65 | — | 90 | — |
| 8 | 50 | — | 100 | 90 |
| 9 | 50 | — | 100 | — |
| 35 | — | — | 60 | 90 |
| 47 | 70 | — | — | — |
| 48 | 70 | — | — | — |
| 78 | 10 | — | — | 100 |
| 29 | 75 | 70 | 100 | 30 |
| 32 | 30 | 70 | 100 | 55 |
| 41 | 80 | — | 100 | 80 |
| 42 | 80 | — | 100 | 90 |
| 36 | 30 | 55 | 100 | 70 |
| 28 | 85 | 70 | 100 | 40 |
| 5 | 100 | 95 | 80 | 100 |
| 19 | 95 | 90 | 100 | 95 |
| 46 | 95 | 95 | 100 | 80 |
| 15 | 75 | 70 | 100 | 45 |
| 52 | 100 | — | 100 | 65 |
| 21 | 65 | 45 | 95 | 55 |
| 33 | 100 | 100 | 100 | 95 |
| 38 | 75 | 65 | 100 | 100 |
| 38 | 75 | — | 100 | 100 |
| 53 | 100 | — | 100 | 65 |
| 82 | 75 | — | 100 | 65 |
| 84 | 80 | — | 100 | 65 |
| 86 | 100 | — | 100 | 85 |
| 91 | 65 | — | 90 | 55 |
| 43 | — | — | 100 | 55 |
| 4 | 100 | 20 | 50 | — |
| 59 | 80 | — | — | 40 |
| 7 | 20 | — | 100 | 50 |
| 58 | — | — | 90 | 45 |
| 17 | 80 | 70 | 30 | 30 |
| 24 | 95 | 90 | 100 | 95 |
| 21 | 45 | 5 | 85 | 25 |
| 44 | — | 100 | 100 | 60 |
| 53 | 90 | — | 60 | 50 |
| 57 | 65 | — | 100 | 60 |
| 65 | 95 | — | 75 | 85 |
| 77 | 75 | — | 80 | 60 |
| 81 | 60 | — | 70 | 75 |
| 85 | 90 | — | 100 | 65 |

EXAMPLE 26

Foliar Spray for protecting plants from infection by the peanut leafspot fungus, *Cercospora arachidicola*.

Test procedure

The chemical suspensions were prepared in a manner described in Example 23. The suspensions were sprayed on duplicate pots of clustered one-month old peanut plants (variety Florrunner), using a gun-type sprayer. After the plants were dried, they were inoculated with the fungus by spraying with a suspension of *Cercospora arachidicola* spores (20,000 spores/ml) to which a standard wetting agent had been added (Tween 20, 6 drops/300 ml). Plants were placed in temperature-humidity controlled chamber for 24–48 hours at 70° F. (21° C.) to allow infection to be initiated. Plants were then removed from the chamber and transferred to a 70° F. (21° C.) greenhouse to allow disease development. After about 21 days, symptoms had developed on the leaflets. Disease control was evaluated by counting lesions if infection was moderate or evaluating by a disease rating scale of 0–6, with 6 being severe disease. Percent control was computed by comparing the treatment scores with that of the untreated control. The results are shown in TABLE 13.

TABLE 13

Control of Cercospora Leafspot Disease of Peanuts by Foliar Application

| COMPOUND | PPM | % DISEASE CONTROL |
|---|---|---|
| 65 | 1000 | 95 |
| | 500 | 90 |
| 77 | 1000 | 93 |
| | 500 | 95 |
| 84 | 1000 | 100 |
| | 500 | 100 |
| 67 | 1000 | 80 |
| | 500 | 45 |
| 68 | 1000 | 85 |
| | 500 | 80 |
| 72 | 1000 | 78 |
| | 500 | 78 |
| 73 | 1000 | 80 |
| | 500 | 75 |
| 75 | 1000 | 50 |
| | 500 | 50 |
| 82 | 1000 | 90 |
| | 5000 | 80 |
| 83 | 1000 | 90 |
| | 500 | 95 |
| 90 | 1000 | 96 |
| | 500 | 92 |
| 95 | 1000 | 55 |
| | 5000 | 55 |
| 97 | 1000 | 80 |
| | 500 | 90 |

What is claimed is:

1. A method of defoliating plants comprising applying to the plants a defoliating amount of a compound having the formula:

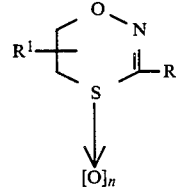

wherein
n = 0, 1 or 2
$R^1$ = hydrogen, $C_1$–$C_4$ linear or branched alkyl, or benzyl with the provisos that:
if n = 0, 1 or 2,
R = phenyl or naphthyl
phenyl substituted with 1 or 2 members selected from the group consisting of:
3- or 4-halo
3,5-dichloro
2-($C_1$–$C_4$ alkyl)
4-($C_3$–$C_4$ alkyl)
2,5-dimethyl
phenyl
3-methoxy
4-($C_2$–$C_5$ alkoxy)
$C_2$–$C_5$ alkylcarbonyl
3- or 4-carboxy, alkali metal salt
3- or 4-methoxycarbonyl
$C_2$–$C_5$ alkylaminocarbonyl
phenylaminocarbonyl
3-cyano
amino and
3-nitro;
3- or 4-pyridinyl; or
furanyl;

if n=0 or 1,
  R=phenyl substituted with:
    2-halo
    2,4-dihalo
    2,5-dimethyl
    4-$CF_3$
    3-pentyloxy
    3-($C_2$–$C_3$ alkoxycarbonyl) or
    morpholinocarbonyl; or
    thienyl;
if n=1 or 2,
  R=phenyl substituted with:
    3-$CF_3$
    4-methoxy
    4-nitro
    4-nitrotolyl or
    3,4-dichloro;
if n=0,
  R=phenyl substituted with:
    2-halo
    3-methyl
    3,5-dimethyl or
    phenoxy;
  furanyl substituted with methyl and ethoxy, or carbonyl;
if n=1,
  R=phenyl substituted with:
    2,6-dichloro
    4-$CH_3$ or
    4-ethoxycarbonyl;
if n=0 or 2,
  R=phenyl substituted with tolylaminocarbonyl.

2. A method as in claim 1 in which $R^1$ is hydrogen or $C_1$–$C_4$ linear or branched alkyl with the provisos that:
if n=0, 1 or 2,
  R=phenyl substituted with:
    3-halo
    3,5-dichloro
    3-methoxy
    4-carboxy alkali metal salt
    3-amino
    3-nitro
    3-cyano;
  3- or 4-pyridinyl;
if n=0 or 1,
  R=phenyl substituted with:
    2-halo
    4-(Br or Cl)
    2,4-dichloro
    2,5-dimethyl
    2-thienyl
if n=1 or 2,
  R=phenyl substituted with:
    3-CF
    3-$CH_3$-4-$NO_2$
    4-nitro
    4-methoxy;
if n=0,
  R=phenyl subsituted with:
    phenoxy;
if n=1,
  R=phenyl substituted with:
    $C_2$–$C_4$ alkoxy
    4-($C_1$–$C_4$ n-alkyl)
    4-methylcarbonyl
    3-($C_2C_3$ alkoxycarbonyl) P3 4-methoxycarbonyl.

3. A method as in claim 1 in which the said compound is the comound of claim 1 wherein $R^1$ is hydrogen or methyl, n is 0, 1 or 2 and R is phenyl substituted with 3-Cl, 3-Br, 3-F, 2,5-dimethyl, 3-trifluoromethyl, 3-nitro or 3-cyano.

4. A method as in claim 1 in which the said compound is the compound of claim 10 wherein n is 1, $R^1$ is hydrogen and R is 3-fluorophenyl.

5. A process in accordance with claim 1 wherein R is 3-halophenyl.

6. A process in accordance with claim 5 wherein R is 3-chlorophenyl.

7. A process in accordance with claim 5 wherein $R^1$ is hydrogen; n is 0; and R is 3-chlorophenyl.

8. A process in accordance with claim 5 wherein $R^1$ is hydrogn; n is 1; and R is 3-chlorophenyl.

9. A process in accordance with claim 5 wherein $R^1$ is 6-methyl; n is 1; and R is 2-fluorophenyl.

* * * * *